US008877267B2

(12) United States Patent
Astrup et al.

(10) Patent No.: US 8,877,267 B2
(45) Date of Patent: Nov. 4, 2014

(54) FLAXSEEDS FOR BODY WEIGHT MANAGEMENT (75) Inventors: Arne Vernon Astrup, Klampenborg (DK); Inge Tetens, Ballerup (DK); Agnete Dal Thomsen, Viby J (DK)

(73) Assignee: University of Copenhagen, Copenhagen N (DK)

( * ) Notice: Subject to any disclaimer, the term of this patent is extended or adjusted under 35 U.S.C. 154(b) by 24 days.

(21) Appl. No.: 11/579,794

(22) PCT Filed: May 10, 2005

(86) PCT No.: PCT/DK2005/000314
§ 371 (c)(1),
(2), (4) Date: Jul. 2, 2007

(87) PCT Pub. No.: WO2005/107777
PCT Pub. Date: Nov. 17, 2005

(65) Prior Publication Data
US 2007/0292542 A1 Dec. 20, 2007

Related U.S. Application Data (60) Provisional application No. 60/569,252, filed on May 10, 2004.

(30) Foreign Application Priority Data

May 10, 2004 (DK) .................................. 2004 00742

(51) Int. Cl.
*A61K 36/55* (2006.01)
*A61K 36/00* (2006.01)
*A23L 2/00* (2006.01)
*A21D 13/02* (2006.01)
*A21D 2/26* (2006.01)
*A21D 2/36* (2006.01)
*A23L 1/10* (2006.01)
*A21D 13/04* (2006.01)

(52) U.S. Cl.
CPC .............. *A21D 2/266* (2013.01); *A23V 2002/00* (2013.01); *A21D 13/02* (2013.01); *A21D 2/36* (2013.01); *A61K 36/55* (2013.01); *A23L 1/10* (2013.01); *A23L 1/1016* (2013.01); *A21D 13/04* (2013.01)
USPC ............................. 424/768; 424/725; 426/590

(58) Field of Classification Search
None
See application file for complete search history.

(56) References Cited

U.S. PATENT DOCUMENTS

| 4,598,089 A | 7/1986 | Hadvary et al. |
| 4,857,326 A | 8/1989 | Stitt |
| 5,110,592 A * | 5/1992 | Stitt ................................ 424/768 |
| 5,612,074 A | 3/1997 | Leach |
| 5,643,874 A | 7/1997 | Bremer et al. |
| 6,475,530 B1 * | 11/2002 | Kuhrts ........................... 424/725 |
| 6,579,544 B1 | 6/2003 | Rosenberg et al. |
| 2002/0091110 A1 * | 7/2002 | Bruckner et al. ............. 514/171 |
| 2004/0171694 A1 * | 9/2004 | Van Laere et al. ............ 514/574 |
| 2004/0241134 A1 * | 12/2004 | Adams .......................... 424/78.1 |

FOREIGN PATENT DOCUMENTS

| CA | 510186D | 2/1955 |
| CN | 1426702 A | 7/2003 |
| DE | 37 39 700 A1 | 6/1989 |
| EP | 1 491 099 A1 | 12/2004 |
| EP | 1 679 009 A1 | 7/2006 |
| GB | 535321 | 4/1941 |
| GB | 2 008 408 A | 6/1979 |
| JP | 1197440 A | 8/1989 |
| JP | 2001-275613 | 10/2001 |
| JP | 2002047194 A | 2/2002 |
| JP | 2002-536988 | 11/2002 |
| JP | 2003-528642 | 9/2003 |
| JP | 2004083428 A | 3/2004 |
| WO | WO 93/21774 | 11/1993 |
| WO | WO 97/35594 | * 10/1997 |
| WO | WO 99/33450 | 7/1999 |
| WO | WO 00/19842 | 4/2000 |
| WO | WO 00/19842 A1 | 4/2000 |
| WO | WO 00/49896 A1 | 8/2000 |
| WO | WO 01/74179 A1 | 10/2001 |
| WO | WO 2009/033483 A1 | 3/2009 |

OTHER PUBLICATIONS

Bhathena et al, Dietary flaxseed meal is more protective than soy protein concentrate against hypertriglyceridemia and steatosis of the liver in an animal model of obesity, Journal of the American College of Nutrition 22 (2): 157-164, 2003.*
Sosulski et al, Composition and physiological properties of several sources of dietary fiber, Journal of food science, 47: 1472-1477, 1982.*
Mazza et al, Flaxseed, dietary fiber, and cyanogens, Flaxseed in human nutrition/editors, Stephen C. et al, AOCS Press Champaign, ILL. 1995: 56-81.*
Enzi et al, Effect of a hydrophilic mucilage in the treatment of obese patients, Pharmatherapeutica 1980; 2 (7): 421-8.*
Jenkins et al, Health aspects of partially defatted flaxseed, including effects on serum lipids, oxidative measures, and ex vivo androgen and progestin activity: a controlled crossover trial, Am J Clin Nutr 1999; 69: 395-402.*
Bhathena, et al. 2002. Effects of dietary soybean and flaxseed meal on metabolic parameters in a genetic model of obesity and diabetes. *Experimental Biology 2002: Meeting Abstracts*, p. A1013, XP008050724.

(Continued)

*Primary Examiner* — Qiuwen Mi
(74) *Attorney, Agent, or Firm* — McLane, Graf, Raulerson & Middleton, PA (57) ABSTRACT

The present invention relates to methods for reducing fat uptake in the gastrointestinal tract of a mammal in order to prevent a positive energy balance, weight gain, overweight and obesity, and to induce a negative energy balance and weight loss in subjects who wish to reduce their body weight. In particular, food and/or beverage ingredients and dietary supplements of the present invention comprises flaxseeds useful for increasing faeca fat excretion from the gastrointestinal tract.

36 Claims, 1 Drawing Sheet

(56) References Cited

OTHER PUBLICATIONS

Bligh, et al. 1959. A rapid method of total lipid extraction and purification. *Canadian Journal of Biochemistry and Physiology*, 37(8):911-917.
Cummings, et al. 1976. Transit through the gut measured by analysis of a single stool. *Gut*, 17:219-223.
Cunnane, et al. 1993. High α-linolenic acid flaxseed (*Linum usitatissimum*): Some nutritional properties in humans. *British Journal of Nutrition*, 69:443-453.
Frotz, et al. 1969. Die Veränderungen des Stuhlfettsäuremusters nach Leinölbelastung und ihr diagnostischer Wert zur Beurteilung der Fettresorption. *Varhandlungen der Deutchen Gesellschaft fur innere medizin*, vol. 75, pp. 666-669.
Kleiber, M. 1987. The Fire of Life: An Introduction to Animal Energetics (pp. 259-264). New York: John Wiley.
Knudsen, K. E. B. 1997. Carbohydrate and lignin contents of plant materials used in animal feeding. Animal Feed Science Technology, 67:319-338.
Livesey, .G. 1989. Procedure for calculating the digestible and metabolisable energy values of food components making a small contribution to dietary intake. *J. Sci. Food Agric.*, 48:475-481.
Livesey, G. 1990. Energy values of unavailable carbohydrate and diets: An inquiry and analysis. *Am. J. Clin. Nutr.*, 51:617-637.
Lucas, et al. 2004. Flaxseed reduces plasma cholesterol and atherosclerotic lesion formation in ovariectomized Golden Syrian hamsters. *Atherosclerosis*, 173:223-229.
Madhusudhan, et al. 1985. Effect of heat treatment on the functional properties of linseed meal. *J. Agric. Food Chem.*, 33:1222-1226.
Oomah, B. D. 2001. Flaxseed as a functional food source. *Journal of the Science of Food and Agriculture*, 81:889-894.
Ortiz, et al. 2001. Metabolisable energy value and digestibility of fat and fatty acids in linseed determined with growing broiler chickens. *British Poultry Science*, 42:57-63.
Rodriguez, et al. 2001. Effect of inclusion level of linseed on the nutrient utilisation of diets for growing broiler chickens. *British Poultry Science*, 42:368-375.
Sandström, et al. 2000. A high oat-bran intake does not impair zinc absorption in humans when added to a low-fiber animal protein-based diet. *The Journal of Nutrition*, 130:594-599.
Velasquez, et al. 2003. Dietary flaxseed meal reduces proteinuria and ameliorates nephropathy in an animal model of type II diabetes mellitus. *Kidney Internationa*, 64:2100-2107.
Wisker, et al. 1992. Contribution of barley fiber to the metabolizable energy of human diets. *Nutrition Research*, 12:1315-1323.
Beændegaard, Mikkelsen, Euroman, Mar. 2003, No. 109, pp. 138-139.
Forbrugernyt, Something to Munch on, Samvirke, Nov. 2003, 26(11): 112.
Hansen et al., The Nutritional Influence of Flax Seed and Sunflower Seeds in Rye Bread, Tine Worm Damgaards, Sep. 17, 2002, pp. 1-4.
Krotkiewski et al., Effect d'une Preparation a Base de Galactoniannane sur le Rassasiement, la Satiété, la Faim et les Préférences Alimentaires chez des Femmes Obèses Suivant un Régime Hypocalorique de 1100kcal/jour, Cahiers de Nutrition et de Dietetique, 1992, 27(4), 211-17.
Schulstad et al., Bread and Health, article on homepage at http://www.schulstad.dk/external/schulstad/webbuilder.nsf/0/01ad66cda6fle879c1256d . . . , dated Dec. 15, 2003.
Wolever et al., Effect of Dietary Fiber and Foods on Carbohydrate Metabolism, CRC handbook of Dietary Fiber in Human Nutrition 3$^{rd}$ Edition, CRC Press, 2001, pp. 321-360.
FAO/WHO, FAO/WHO/UNU, Energy and Protein Requirements, Technical Report Series 724, World Health Organization, Geneva, 1985. http://www.fao.org/docrep/003/AA040E/AA040E00.HTM.
International Search Report dated Aug. 5, 2005, cited in International application No. PCT/DK2005/000314.
International Search Report and Written Opinion dated Dec. 19, 2008 for PCT/DK2008/000321.

Bansal, Sandeep et al., "Fasting Compared With Nonfasting Triglycerides and Risk of Cardiovascular Events in Women" JAMA, Jul. 18, 2007, pp. 319-316, vol. 298, No. 3.
Bellisle, F. "Functional Foods and the Satiety Cascade" British Nutrition Foundation, 2008, pp. 8-14, vol. 33.
Flint, A. et al., "Reproducibility, power and validity of visual analogue scales in assessment of appetite sensations in single test meal studies" International Journal of Obesity, 2000, pp. 38-48, vol. 24.
Oomah, B. Dave et al., "Fractionation of flaxseed with a batch dehuller" Industrial Crops and Products, 1998, pp. 19-27, vol. 9.
Oomah, B. Dave et al., "Health benefits of phytochemicals from selected Canadian crops" Trend in Food Science and Technology, 1999, pp. 193-198, vol. 10.
Ibrügger, Sabine et al., "Flaxseed dietary fiber supplements for suppression of appetite and food intake" Appetite, 2012, pp. 490-495, vol. 58.
Kristensen, M. et al., "Whole flaxseeds but not sunflower seeds in rye bread reduce apparent digestibility of fat in healthy volunteers" European Journal of Clinical Nutrition, 2008, pp. 961-967, vol. 62.
Kristensen, M. et al., "Flaxseed dietary fibers suppress postprandial lipemia and appetite sensation in young men" Nutrition, Metabolism & Cardiovascular Diseases, 2011, pp. 1-8.
Kristensen, Mette et al., "Flaxseed dietary fibers lower cholesterol and increase fecal fat excretion, but magnitude of effect depend on food type" Nutrition & Metabolism, 2012, pp. 1-8, vol. 9.
Kristensen, M. et al., "Whole flaxseeds but not sunflower seeds in rye bread reduce apparent digestibility of fat in healthy volunteers" European Journal of Clinical Nutrition, May 23, 2007, pp. 1-7.
Scheideler, Dr. Sheila E. et al., "Use of Enzymes in Poultry Rations Containing Flaxseed" Dept. of Animal Sci., University of Nebraska, 1996, pp. 97-100.
Alzueta, C. et al., "Effect of whole and demucilaged linseed in broiler chicken diets on digesta viscosity, nutrient utilization and intestinal microflora" British Poultry Science, 2003, pp. 67-74, vol. 44.
Kempe, R. et al., "Effect of linseed cake supplementation on digestibility and faecal and haematological parameters in dogs" Journal of Animal Physiology and Animal Nutrition, 2007, pp. 319-325, vol. 91.
Kristensen, Mette "Wholegrains and dietary fibres—Impact on body weight, appetite regulation and nutrient digestibility" PhD Thesis, Department of Human Nutrition, Faculty of Life Sciences, University of Copenhagen, Denmark 2009.
Thakur, Goutam et al., "Effect of flaxseed gum on reduction of blood glucose and cholesterol in type 2 diabetic patients" International Journal of Food Sciences and Nutrition, 2009, pp. 1-11.
Turnbull, Wh et al., "The effect of a *Plantago ovata* seed containing preparation on appetite variables, nutrient and energy intake" International Journal of Obesity, 1995, pp. 338-342, vol. 19.
Ascherio, Alberto "Trans fatty acids and blood lipids" Atherosclerosis Supplements, 2006, pp. 25-27, vol. 7.
Crespo, N. et al., "Dietary Polyunsaturated Fatty Acids Decrease Fat Deposition in Separable Fat Depots but Not in the Remainder Carcass" Poultry Science, Apr. 2002, pp. 512-518, vol. 81, No. 4.
Crespo, N. et al., "Nutrient and Fatty Acid Deposition in Broilers Fed Different Dietary Fatty Acid Profiles" Poultry Science, Oct. 2002, pp. 1533-1542, vol. 81, No. 10.
Jenkins, David J.A. "Dietary Fibre, Diabetes, and Hyperlipidaemia—Progress and Prospects" The Lancet, Dec. 15, 1979, pp. 1287-1290.
Jenkins, David J.A. et al., "Low glycemic index carbohydrate foods in the management of hyperlipidemia" The American Journal of Clinical Nutrition, Oct. 1985, pp. 604-617.
Katan, Martikin B. et al., "Effects of fats and fatty acid on blood lipids in humans: an overview" Am J Clin Nutr, 1994, pp. 1017S-1022S, vol. 60(suppl.).
Miller, Edgar R. et al., "The Effects of Macronutrients on Blood Pressure and lipids: An Overview of the Dash and OmniHeart Trials" Current Atherosclerosis Reports, 2006, pp. 460-465, vol. 8.

\* cited by examiner

FLAXSEEDS FOR BODY WEIGHT MANAGEMENT

CROSS REFERENCE TO RELATED APPLICATION

This application claims the benefit and priority to and is a U.S. National Phase of PCT International Application Number PCT/DK2005/000314, filed on May 10, 2005, designating the United States of America and published in the English language, which claims priority under 35 U.S.C. §119 to Danish Application Number PA 2004 00742 filed on May 10, 2004 and to U.S. Application No. 60/569,252 filed on May 10, 2004. The disclosures of the above-referenced applications are hereby expressly incorporated by reference in their entireties.

FIELD OF THE INVENTION

The present invention relates to methods, food ingredients and dietary supplements for body weight management i.e. prevention of a positive energy balance, weight gain and overweight, treatment of overweight and obesity as well as fat reduction for cosmetic purposes. In particular, the food ingredient and dietary supplements of the present invention comprises flaxseeds useful for reducing fat uptake in the gastrointestinal tract and to induce a negative energy balance and weight loss in subjects who wish to reduce their body weight.

BACKGROUND OF THE INVENTION

The current way of life in industrialised countries may be characterised by less physical work and increased consumption of fat and carbohydrates, resulting in the energy intake exceeding energy expenditure. This shift in the energy balance causes storage of energy in the body in form of fat, leading to an increase of overweight and obesity, due to the long-term energy imbalance associated with lifestyle.

The percentage of overweight people increases year by year and obesity is a disease that is reaching epidemic proportions in some countries. The health risks associated with overweight and obesity are numerous and it has been shown that these conditions contribute to morbidity and mortality of individuals suffering from diseases such as hypertension, stroke, diabetes mellitus type II, gallbladder disease and ischaemic heart disease. The cosmetic perspective of body fat is also to be considered as the demand for dietary supplements or medicine to gain or maintain a leaner body is constantly increasing.

A common strategy for reducing the risk of overweight and obesity has been to reduce the average energy intake by lowering the dietary fat intake. Dietary fat is a major determinant for energy density of the diet and thereby for energy intake. A reduction in the daily consumption of fat concurrently, with an increase in the consumption of foods rich in complex carbohydrates, is part of the dietary recommendations in many countries.

An additional strategy may be to consume foods with a low digestibility. It is well established that the dietary fibre content of the diet is an important determinant of the digestibility of energy and energy-contributing macro-nutrients. It has been suggested that increasing amounts of dietary fibres in the food promotes satiety and thereby reduces energy intake, and decreases transit time of ingested food in the intestinal tract.

Another strategy for weight management is to reduce fat absorption from the gastrointestinal tract by using various kinds of medicaments. Fat is mainly consumed in the form of triglycerides and pancreatic lipases are required to break down the triglycerides into monoglycerides and fatty acids in order for the body to absorb the fat from the gastrointestinal tract. U.S. Pat. No. 4,598,089 disclose the compounds lipstatin and tetrahydrolipstatin, which reduce fat absorption by inhibiting pancreatic lipase. WO9933450 discloses the weight loss effect of sibutramine and orlistat, where sibutramine promotes decreased food intake by enhancing satiety and orlistat inhibits lipases from breaking down ingested fat. U.S. Pat. No. 5,643,874 discloses a composition comprising both glucosidase/amylase inhibitors such as acarbose or voglibose and lipase inhibitors such as orlistat or lipstatin for treatment of obesity. However, in view of the complexity of the genetic component of obesity and the various psychological factors involved in maintaining lifestyle habits, the long term efficacy of such medicaments in managing body weight and decreasing obesity-related medical complications is unknown.

SUMMARY OF THE INVENTION

Thus, identification of alternative therapeutic regimens remains desirable for treatment and prevention of overweight. The present inventors have found that administration of an effective amount of a flaxseed product, in particular whole processed flaxseeds, are effective for reducing fat uptake in the gastrointestinal tract of a mammal in order to prevent a positive energy balance, weight gain, overweight and obesity, and to induce a negative energy balance and weight loss in subjects who wish to reduce their body weight. Accordingly, the present invention provides methods, food and/or beverage ingredients and dietary supplements comprising flaxseeds useful for increasing faecal fat excretion from the gastrointestinal tract in mammals including humans.

Accordingly, in a first aspect the invention relates to the use of a flaxseed product in the preparation of a food and/or beverage product for increasing faecal fat excretion from the intestinal tract in a mammal, from said flaxseed product and/or other foods and/or beverages ingested prior, concomitantly or immediately after said flaxseed product.

A further aspect relates to the use of a flaxseed product for increasing faecal fat excretion from the intestinal tract in a mammal, from a food and/or beverage product having a fat content of at least 7% by weight of said food and/or beverage product, ingested prior, concomitantly or immediately after said flaxseed product.

In a still further aspect there is provided a high fat content food and/or beverage product having a fat content of at least 7% by weight, comprising a total content of a flaxseed product which corresponds to a content of 1 to 50% by weight of flaxseed products.

Further, the present invention provides a method of increasing faecal fat excretion, in a mammal, from ingested food and/or beverage products comprising, administering prior, concomitantly or immediately after ingesting of said food and/or beverage product an effective amount of a flaxseed product.

In a further aspect, there is provided a method of treating obesity comprising administering to a person suffering from obesity an effective amount of a composition comprising a flaxseed product.

A still further aspect of the present invention provides a method for the cosmetic treatment or prevention of overweight which comprises orally administrating an effective amount of a flaxseed product or a composition comprising a flaxseed product.

Moreover, the present invention relates to the use of hydrated and/or heat-treated flaxseed for treatment or prevention of cosmetic overweight.

A further aspect of the present invention relates to the use of hydrated and/or heat treated flaxseed as a food ingredient or a dietary supplement for increasing faecal fat excretion in a mammal.

In still a further aspect the invention relates to the use of a flaxseed product for the preparation of a composition, wherein the composition is formulated for orally administrating an effective amount of said flaxseed product for the treatment or prevention of cosmetic overweight, medical overweight or obesity.

Further, the invention relates to a method of preventing and/or reducing overweight or obesity in a subject, said method comprising administering a composition comprising a flaxseed product and/or the food and/or beverage product comprising a flaxseed product of the invention to said subject.

Finally, the invention relates to a method of treating obesity comprising administering to a person suffering from obesity an effective amount of a composition comprising a flaxseed product.

DETAILED DESCRIPTION OF THE INVENTION

Flaxseeds are rich in dietary fibre (28 g/100 g) and at the same time contain a high amount of dietary fat (34 g/100 g). Flaxseeds are often added to commonly consumed foods like bread and muffins where they add moisture and taste and thereby contribute to the palatability of the final product. Furthermore, flaxseeds have been identified as the most abundant source of plant lignans known making the dietary intake of flaxseeds of interest from a health promoting point of view. Hence, flaxseeds have been used as dietary supplement in several food products. U.S. Pat. No. 5,612,074 discloses the use of flaxseeds as a constituent in non-cooked food bars and WO0019842 discloses the use of flaxseed fibres and linseed oil from flaxseeds in meat products to provide healthy oil in the diet as well as fibres. Furthermore, a method of producing stable suspensions of grinned flaxseeds has been described in U.S. Pat. No. 4,857,326. The suspensions are particular useful for lowering serum cholesterol due to the availability of healthy oils in the stable suspension. Thus, use of flaxseed as a dietary ingredient for promoting taste of the food and/or for providing fibres, and for providing healthy oils are known in the art.

It was however highly surprising that flaxseed, when used according to the present invention, was found to increase faecal fat excretion, i.e. reduce uptake of fat from the intestinal tract and thus to prevent a positive energy balance and/or to induce a negative energy balance in the subjects who wish to reduce their body weight, as described below. This finding provided basis for use of flaxseed products for overall management of body weight including the treatment and prevention of overweight in mammals such as humans. In the present context, the term "prevention" means that the use of a flaxseed product as defined herein counteracts the start of overweight and obesity, or counteracts a positive energy balance leading to weight gain, or that overweight and obesity at least develop to a minor degree in a subject ingesting a flaxseed product compared to a subject not ingesting a flaxseed product.

In the present context the term "management of body weight" covers all aspect of modulating the body weight for maintenance or achievement of a "desirable weight". In contrast to the "desirable weight" the expressions "overweight" and "obesity" are used as indications of a body with a weight exceeding the "desirable weight".

The "desirable weight", "normal weight" or "optimal weight" for humans may be defined according to standards such as Body Mass Index (BMI), which is a common measure expressing the relationship (or ratio) of weight-to-height (for definition see below). The BMI is more highly correlated with body fat than any other simple measure of height and weight. Desirable BMI levels may vary with age, but a "normal" BMI is considered to be in the range of 18.5-24.9.

The definition of "overweight" is an increased body weight in relation to height, when compared to a standard of acceptable or desirable weight. Individuals with BMI in the range of 25-29.9 are considered to be overweight.

Obesity is a multi-factorial disease involving an accumulation of excess adipose tissue (fat) sufficient to harm health. As stated, overweight and obesity cause the development of several diseases and individuals suffering from overweight or obesity generally have a poor health status. Obesity is largely preventable through changes in lifestyle, especially diet, however, real treatment may be desired and needed to aid in loosing of weight.

There are many types of obesity, but it is most commonly assessed by a single measure, the Body Mass Index (BMI) a ratio of weight and height (BMI=weight (kg)/height (m)$^2$). The World Health Organization classifies underweight, normal weight, overweight and obesity according to categories of BMI (cf. table below). This height independent measure of weight allows comparisons to be made more readily within and between populations. The BMI value, however, neither distinguish fat from lean tissue nor identify whether the fat is laid down in particular sites e.g., abdominally where it has more serious consequences.

Waist circumference measurement is also increasingly recognised as a simple means of identifying abdominal obesity. Body fat distribution can be estimated by skinfold measures, waist-to-hip circumference ratios, or techniques such as ultrasound, computed tomography, or magnetic resonance imaging.

TABLE 1

| Classification | BMI (kg/m$^2$) | Risk of co-morbidities |
|---|---|---|
| Underweight | <18.5 | Low (but risk of other clinical problems increased) |
| Normal range | 18.5-24.9 | Average |
| Overweight* | ≥25 | |
| Pre-obese | 25.0-29.9 | Mildly increased |
| Obese | >30.0 | |
| Class I | 30.0-34.9 | Moderate |
| Class II | 35.0-39.9 | Severe |
| Class III | >40.0 | Very severe |

*The term overweight refers to a BMI ≥ 25, but is frequently and also in the present specification and claims adapted to refer to the BMI 25-29.9, differentiating the pre-obese from the obese categories As illustrated in Table 1 above, the severities of obesity may by classified by ranges of BMI where BMI in the range of 30-34.9 is classified as moderate obesity, BMI in the range of 35-39.9 is classified as severe obesity and BMI over 40 is classified as very severe obesity. The definition of obesity may also include taking in account both the distribution of fat throughout the body and the size of the adipose tissue deposits.

Individuals falling under the above characterisation as "obese" are far more susceptible to health implications as a consequence of their overweight. Several serious medical conditions have been linked to obesity, including type 2 diabetes, heart disease, high blood pressure, and stroke. Obesity is also linked to higher rates of certain types of cancer. Obese men are more likely than non-obese men to die from cancer of the colon, rectum, or prostate. Obese women are more likely than non-obese women to die from cancer of the gallbladder, breast, uterus, cervix, or ovaries. Other diseases and health problems linked to obesity include gallbladder disease and gallstones, liver disease, osteoarthritis, a disease in which the joints deteriorate possibly as a result of excess weight on the joints, gout, another disease affecting the joints, pulmonary (breathing) problems, including sleep apnea in which a person can stop breathing for a short time during sleep, reproductive problems in women, including menstrual irregularities and infertility. Health care providers generally agree that the more obese a person is, the more likely he or she is to develop health problems.

The expression "cosmetic overweight" refers to a weight that does not have any immediately medical implications on the individual but may be in a range that is not satisfactory for cosmetic reasons. As fashion with respect to body size changes some individuals may interpret the "normal weight" as "cosmetic overweight". As a consequence such individuals may have a desire of treating cosmetic overweight.

The expression "fat digestibility" is used herein interchangeably with the expression "fat absorption", "uptake of fat", "fat binding" and "fat digestion". The present inventors surprisingly found, that administration of the flaxseed product as defined herein to an individual highly affected the faecal fat excretion i.e. faecal fat excretion exceeded the fat intake (resulting from the instant flaxseed product or from the concomitantly ingested food and/or beverage product). From experiments (cf. examples of the description) it was evident that the effect could not be ascribed to the known "fibre effect". Hence, the flaxseed product of the present invention demonstrates a "fat retaining capacity" that inherently influences fat digestibility.

In the present context the expression "fat retaining capacity" and "increased fat excretion" is used interchangeably to address the characteristics of the flaxseed product of the present invention. The fat retaining capacity/increased fat excretion are conveniently measured by comparing faecal fat excretion in individuals given a diet comprising the flaxseed product with a control group given a similar diet without the flaxseed product. The fat retaining effect of the flaxseed product may be quantified by calculating the partial digestible energy value as defined hereinafter. A specific test for determining if a given flaxseed product or a flaxseed enriched food product has the capability of increasing the fat excretion could be as follows: The addition of 18 gram of a given flaxseed product to a diet in a mammal increases the faecal fat and energy excretion by at least 14 gram fat/day compared to a control diet similar with respect to macronutrient and energy content but without the addition of a flaxseed product as described herein. Preferably, the increase is higher such as at least 15 gram fat/day, including at least 20 gram fat/day or at least 140 kcal/day, such as at least 280 kcal/day, including at least 420 kcal/day as compared to a control diet similar with respect to macronutrient, energy and fibre content but without the addition of a flaxseed product as described herein. The demonstrated effect of the present flaxseed product and the possibility of formulating the active ingredient in various ways offer obvious possibilities of using flaxseed products for the management of body weight.

The term "fibre effect" is used herein to refer to the physiological effect of dietary fibre intake on digestion and satiety. Soluble dietary or complex fibres increase many times in volume when they mix with fluid and therefore promote satiety. Furthermore, a diet rich in insoluble dietary fibres may decrease transit time (mouth to anus) of ingested food and/or beverages in the intestinal tract. The total dietary fibre effect is therefore that total dietary fibre intake may decrease energy intake by contributing to fullness or satiation and maintaining between meals a feeling of satiety and by decreasing transit time and decreasing energy uptake.

The term "partial digestible energy value" used herein refers to differences in overall digestible nutrients when a supplement is added to a basal diet. The calculation of the partial digestible energy values for unavailable carbohydrates in a number of human diets have been found to be in the range from −20 to +10 kJ/g unavailable carbohydrates. Negative values may refer to the additional losses of especially protein and fat to feces associated with diets high in unavailable carbohydrates. An example of the calculation of partial digestible energy value is described in the below Examples.

In the present context the terms "flaxseed product" and "active ingredient" refer to whole flaxseed and/or any fraction of flaxseed and/or any flaxseed derived material that demonstrate a "fat retaining capacity". More specifically, the expression "whole flaxseed" relates to uninjured, unbroken and/or intact flaxseed, but also to flaxseed flour and grinded and crushed flaxseeds where all the components or parts of the flaxseed are used in the present invention. The expression "a fraction of flaxseed" refers to a component and/or a part of the whole flaxseed and encompasses mucilage, as well as arabinoxylans and galacturonic acid which form part of the mucilage, as described below. However, flaxseed oil or linseed oil do not have a fat retaining capacity, and thus the term "a fraction of flaxseed" does not encompass oil from flaxseed. Accordingly, oil and fat parts of a flaxseed are not within the meaning of the term "flaxseed product" and thus disclaimed from the present invention.

Without being limited by theory, it is contemplated that part of the fat retaining capacity of the flaxseed product and/or active ingredient described herein is a result of the mucilage of the flaxseed. It is hypothesised that a binding may take place between the mucilage of the flaxseed and the fat in the gastrointestinal tract, thereby reducing the overall digestibility of fat. As the mucilage increases heavily upon hydration, the hydration process is important in optimising the fat binding effect. Consequently, the mucilaginous cells represent one very interesting fraction of the flaxseed. Other interesting fractions or flaxseed-derived materials include but are not limited to seed coat including the arabinoxylans and galacturonic acid which form part of the mucilage.

It should be noted that the active ingredient, when in the form of a fraction of flaxseed and/or a flaxseed derived material as previously described, may be derived from other plant species. In particular, plant species containing mucilage capable of binding fat to the gastrointestinal tract of a mammal and which fulfill the conditions described in the above test are also within the scope of the present invention. Examples of such plant species are e.g. rye and oat.

The term "pharmaceutical composition" refers to a composition, comprising the flaxseed product as defined herein, formulated for therapeutic use. The pharmaceutical compositions of the present invention may also include substances to reduce hunger and increase satiety and metabolic rate such as green tea, caffeine and ephedrine as well as other substances reducing fat-uptake (increasing faecal fat excretion), decreasing mouth to anus transit time etc. The pharmaceutical composition of the present invention may be formulated in any desired form including but not limited to a food ingredient, a dietary supplement, a herbal compound, a herbal medicine, a powder, a capsule and a tablet.

It will be appreciated that the flaxseed product i.e. the whole flaxseed and/or fraction of flaxseed and/or flaxseed derived material, may be formulated as, and thus having the characteristics of, a pharmaceutical composition as defined above. However, the flaxseed product is equally suited for formulation as a food or beverage product, i.e. a food and/or beverage composition, or a composition comprising said flaxseed product. Thus, the term "formulated" is intended to relate to selection of excipients, carriers, vehicles, diluent, adjuvant, solvents, co-solvents, preservatives, colouring agents, flavouring agents or any combination thereof in the preparation of a composition or in the preparation of a food and/or beverage product using said composition. The term "formulated" further relates to the selection of suitable food and/or beverage ingredients in the preparation of a food or beverage product using the composition.

Preferably, the whole flaxseed and/or fraction of flaxseed of the present invention is processed in order to secure maximum fat retaining capacity. Typically, processing includes hydration and heat-treatment. The flaxseed and/or any fraction hereof may be processed prior to, during or after formulation or use. The hydration process involves hydrating of the flaxseeds and/or any fraction thereof in a humid environment, e.g. water or any other suitable solvent, for a period of time allowing the flaxseed to swell. A typical hydration process comprises hydration in water or an aqueous liquid for a few hours, such as at least 1 hour, at least 2 hours, at least 3 hours such as at least 5 hours at ambient temperature, such as at least 20° C., at least 24° C. or at least 37° C. In useful embodiments, the hydration process comprises hydration of the flaxseed and/or fraction thereof in water or an aqueous liquid for up to 5 hours, such as up to 4 hours, including up to 3 hours, such as up to 2 hours, including up to 1 hour. A hydration process may also be carried out in a composition e.g. a food composition such as a dough, or in the concomitantly ingested food and/or beverage product. Additionally, hydration may be carried out during a fermentation process such as e.g. during the rising of a sourdough or during the fermentation of a milk product, such as yoghurt.

As mentioned the flaxseed product or the compositions of the invention may be processed in any suitable way, provided that the fat retaining capacity of said processed product or composition is retained. Thus, the flaxseed product or the composition may be mechanically prepared by any desired process including milling, grinding, separation etc. and/or physically prepared by hydration, fermentation, heat treatment etc.

In suitable embodiments, the heat-treatment is carried out at a temperature exceeding 60° C. such as exceeding, 70° C., including exceeding 75° C., 80° C., 85° C., 90° C., 95° C., 100° C., 110° C., 130° C., 150° C., 170° C., 190° C., 210° C., 230° C., 250° C., 270° C., 290° C. or even exceeding 300° C. Preferably, the heat-treatment is carried out at a temperature in the range of 150° C.-300° C., such as in the range of 200° C.-250° C.

As stated, a first aspect of the present invention relates to the use of a flaxseed product in the preparation of a food and/or beverage product for increasing faecal fat excretion from the intestinal tract in a mammal, from said flaxseed product and/or other foods and/or beverages ingested prior, concomitantly or immediately after said flaxseed product.

Accordingly, the flaxseed product of the present invention may be used as an integrated part, such as an ingredient or a dietary supplement, of a low fat diet or any other diet aiming at managing body weight as a direct result of an increasing faecal fat excretion. The flaxseed product as defined herein may be administered or taken prior, concomitantly or immediately after ingesting a food and/or beverage product and/or a diet. In the present context, the term "concomitantly" means that the flaxseed product and the food and/or beverage product are ingested within the same meal, e.g. 1-2 hours apart. The term "prior" means in the present context, that flaxseed product is ingested or taken at least 1 hour before the food and/or beverage product is ingested, or visa versa. The term "after" or "immediately after" means in the present context, that flaxseed product is ingested or taken at least 1 hour after the food and/or beverage product is ingested, or visa versa.

Furthermore, the flaxseed product of the present invention may be used as part of a treatment plan for diabetes or cardiovascular diseases. Furthermore, the flaxseed product may be prepared as a food and/or beverage product for increasing faecal fat excretion from the intestinal tract in a mammal, from said product and/or other concomitantly ingested foods and/or beverages.

The use of the flaxseed product is preferably directed to a subject such as a human, but any mammal, such as an animal may also be treated with the flaxseed product as defined herein. In a preferred embodiment, the subject is a mammal or person who wish to reduce their body weight. In a further embodiment, the subjects suffering from overweight, such as cosmetic overweight, or obesity, and are persons having a BMI of at least 25 as shown in the above Table 1. It is contemplated that the method and use of the invention will be particularly beneficial in a subject, who is overweight, non-obese, or obese subject as defined in Table 1.

The flaxseed product of the present invention may comprise whole flaxseeds and/or one or more fractions of flaxseeds and/or any flaxseed derived material derived, as defined above, from one or more variants selected from the group consisting of Golden, Dufferin, Rahab, Verne, Clark, Culbert, culbert79, Flor, Linott, Linton, McGregor, NorLin, NorMAn and combinations thereof.

As described above the flaxseed product of the invention may be processed or treated in any suitable way, provided that the fat retaining capacity of said processed product is retained. Thus, the flaxseed product may be mechanically prepared by any desired process including milling, grinding, separation and/or physically prepared by hydration, fermentation, heat treatment and combinations thereof.

In preferred embodiments, the flaxseed product as used according to the present invention comprises one or more fractions of flaxseeds selected from the group consisting of seed coat, mucilage, arabinoxylans, galacturonic acid and combinations thereof as described in detail above.

As mentioned, it was highly surprising when the inventors of the present invention realised that the observed increased faecal fat excretion did not depend on the fibre effect as defined above, nor did the increased faecal fat excretion depend on a reduced mouth to anus transit time.

In preferred embodiments, the flaxseed product when used according to the present invention is characterised by having a negative partial digestible energy value, as defined above, in the range of from −1 to −40 kJ/g flaxseed product, including a negative partial digestible energy value in the range of from −10 to −30 KJ/g flaxseed product, such as in the range of from −15 to −25 KJ/g flaxseed product. Thus, when e.g. supplying the basal diet with a flaxseed product according to the invention, the faecal fat excretion will exceed the fat intake either from the flaxseed product itself or from the concomitantly ingested food or beverage. In other words, a positive energy balance is prevented and/or a negative energy balance is induced resulting in a weight loss in subjects who wish to reduce their body weight.

In preferred embodiments, the faecal fat excretion will exceed the fat intake by at least 5%, such as at least 10%, including at least 15%, such as at least 20%, such as at least 30%, including at least 40%. In accordance with the present invention, the flaxseed product when consumed together with a food and/or beverage product reduces the fat uptake in the intestinal tract of a mammal consuming the flaxseed product and the food or beverage. In preferred embodiments, the flaxseed product reduces the digestibility of fat present in concomitantly ingested food and/or beverage by 5-10%, preferably, 2-15%, more preferably by 10-18%, most preferably by 20-25%, as calculated by the method used in the below Example 1.

The sufficient daily dose for preventing or treating cosmetic overweight or for treatment of medical overweight or obesity as a result of an increased faecal fat excretion may vary according to the severity of the overweight/obesity as well as the individual variation and need in order to obtain a desired result. Thus, the daily dose of flaxseed or any fragment hereof is equivalent to an amount of 1 to 100 grams of whole flaxseed, such as an amount of 1 to 30 grams, including an amount of 10-20 grams of whole flaxseed. Typically, the daily dose is equivalent to an amount of about 5 grams of whole flaxseed, such as 10 g, 15 g, 20 g, 25 g, 30 g, 35 g, 40 g, 45 g, 50 g, 60 g, 70 g, 80 g or 90 grams of flaxseed. Obviously, the amount as such is much higher if an active fraction of the flaxseed is directly used. The mucilage constitutes between 5 and 8 wt % of the flaxseed, thus a daily dose in an amount of 100-1000 g mucilage may be suitable, such as an amount of 150-800 g, including 250-600 g mucilage.

Thus, a typical intake for increasing the faecal fat excretion and/or for treatment of overweight is a dose equivalent to about 10-25 g whole flaxseed/day resulting in a loss of faecal fat from the normal 4-10% of ingested fat to 15-250%. This corresponds to an additional loss of faecal energy of 10-20 gram fat/day, or 375-750 kJ/day, or 300-600 g body weight per month. In the present context, the expression "an additional loss of faecal energy" relates to a negative partial digestible energy value, and thus to that the total faecal fat excretion exceeds the additional fat intake derived from the flaxseed addition to a considerable extent as described above.

In further embodiments, the total content of a flaxseed product, a fraction of flaxseed or and/or a flaxseed derived material when used according to the invention in a food and/or beverage product typically corresponds to a content of 1 to 50% by weight of flaxseed products, including a content of 1%, 20%, 3%, 4%, 5%, 10%, 15%, 20%, 30% 40% by weight of flaxseed products in the food and/or beverage product. In useful embodiments, the total content of a flaxseed product, a fraction of flaxseed or and/or a flaxseed derived material when used according to the invention in a food and/or beverage product typically corresponds to a content of 5 to 40%, such as 10 to 30%, including 15-25% by weight of flaxseed products.

In useful embodiments, the food and/or beverage product concomitantly consumed with the flaxseed product further comprises ground grains and/or whole grains of one or more of the species selected from the group consisting of sunflower, rye, wheat, maize, soy and combinations thereof. In an interesting embodiment, said food and/or beverage product is included in a low fat diet. In the present context, the expression "low fat diet" relates to a diet which fat content is providing only 10-25% of the total energy intake.

It will be understood from the above, that the food and/or beverage product may be consumed together with the flaxseed product as two separated ingredients in a diet, or the flaxseed product may be added to the food and/or beverage product and thus become an enriched food and/or beverage product. The above food and/or beverage product may preferably be subject to a heat treatment by any conventional method before or after being consumed with the flaxseed product or before or after being mixed with the flaxseed product.

In the examples below, it is shown that when a flaxseed product is incorporated into bread or consumed as part of a whole diet by healthy subjects the flaxseed product has a negative effect on the fat binding in the intestinal tract of the subject. A person skilled in the art will easily appreciate that a flaxseed product according to the invention will have the same effect when used in other food and/or beverage products. Thus, in useful embodiments, the food and/or beverage product has the form of a nutritional bar, a snack bar including a chocolate bar and other sweets, a baked product such as bread, rye bread, biscuit, tea-bisquit, cracker, potato chips, pie-crust, pâté and patty, a milk product such as butter, cream, butter milk, yoghurt, junket, ice-cream, cheese, a vegetable product, a meat product such as liver paste, sausages, meatballs, beef burger, fish cake, a semi-manufactured product and combinations thereof.

Flaxseeds capability of binding the fat of concomitantly ingested food is in particular useful in food and/or beverage products containing a high content of fat. Thus, a useful aspect of the present invention relates to the use of a flaxseed product for increasing faecal fat excretion from the intestinal tract in a mammal, from a food and/or beverage product having a fat content of at least 7% by weight (w/w) of said food and/or beverage product ingested prior, concomitantly or immediately after said flaxseed product. In preferred embodiments, the fat content of the ingested food and/or beverage is at least 10%, such as at least 15%, including at least 20%, e.g. at least 25%, including at least 30% such as at least 40% by weight of the food and/or beverage product.

Certain food and/or beverage products are characterized as unhealthy due to their relatively high fat content. Thus, in a preferred embodiment, the flaxseed product is used as an integrated part for managing body weight in a the food and/or beverage product selected from the group consisting of a nutritional bar, a snack bar including a chocolate bar and other sweets, a baked product such as bread, rye bread, biscuit, tea-biscuit, cracker, potato chips, pie-crust, pâté and patty, a milk product such as butter, cream, yoghurt, butter milk, junket, ice cream, cheese, a vegetable product, a meat product such as liver paste, sausages, meatballs, beef burger, fish cake, a semi-manufactured product and combinations thereof.

As will be apparent, preferred features, characteristics and embodiments of one aspect of the present invention may be applicable to other aspects of the present invention.

Further aspect of the present invention, relates to a high fat content food and/or beverage product having a fat content of at least 7% by weight, comprising a total content of a flaxseed product which corresponds to a content of 1 to 50% by weight of flaxseed products. In useful embodiments, the content of a flaxseed product in the high fat content food and/or beverage product is 1%, 2% 3%, 5%, 10%, 15%, 20%, 30% or 40% by weight of flaxseed products in the food and/or beverage product. In useful embodiments, the total content of a flaxseed product, a fraction of flaxseed or and/or a flaxseed derived material when used according to the invention in the food and/or beverage product typically corresponds to a content of 5 to 40%, such as 10 to 30%, including 15-25% by weight of flaxseed products.

In preferred embodiments, said food and/or beverage product contains at least 9% fat by weight of the product, such as at least 10%, such as at least 15%, including at least 20%, e.g.

at least 25%, including at least 30% such as at least 40% by weight of the food and/or beverage product.

Interesting high fat content food and/or beverage products, wherein the flaxseed is used as an integrated part for managing body weight, are variants of the products described above having a higher content of fat.

It should be understood that any embodiments and/or feature discussed above in connection with the uses of a flaxseed product according to the invention apply by analogy to the below aspects of the present invention.

In a further aspect, the present invention provides a method for increasing faecal fat excretion from the intestinal tract in a mammal, from a food and/or beverage product having a fat content of at least 7% by weight of said food and/or beverage product ingested comprising administering to the mammal prior, concomitantly or immediately after said food and/or beverage product a composition comprising an effective amount of a flaxseed product, as described above.

In a further aspect, the present invention provides a method for preparing a food and/or beverage product for increasing faecal fat excretion from the intestinal tract in a mammal comprising formulating a flaxseed product into the food and/or beverage product.

In a still further aspect, the present invention relates to the use of a flaxseed product, as defined above, for the preparation of a composition, wherein the composition is formulated, as described above, for oral administration of an effective amount of said flaxseed product for the treatment or prevention of cosmetic overweight, medical overweight or obesity. The treatment is preferably directed to a subject such as a human, but any mammal, such as an animal may also be treated with the flaxseed product or any active component hereof as defined herein. Examples of preferred subjects that will benefit from this use of a flaxseed product are outlined in the above Table 1. It is evident that subjects with a BMI above 18.5 and in particular above 25 will benefit of the use of flaxseed.

A further aspect of the present invention, relates to a method of increasing faecal fat excretion, in a mammal, from ingested food and/or beverage products, as defined above, comprising, administering prior, concomitantly or immediately after ingesting of said food and/or beverage product an effective amount, as described above, of a flaxseed product as defined herein.

Another aspect pertains to a method of preventing or treating obesity or preventing or treating cosmetic overweight by administering an effective amount, as described above, of a flaxseed product or composition comprising a flaxseed product as defined herein. The treatment is preferably directed to a subject such as a human, but any mammal, such as an animal may also be treated with the flaxseed product or any active component hereof as defined herein.

In a still further aspect, the present invention relates to a method for the prevention or treatment of a condition selected from the group consisting of overweight, obesity and cosmetic overweight comprising administering to a person suffering from said condition an effective amount, as described above, of a flaxseed product, as defined herein, or a food and/or beverage product, as defined above, comprising flaxseed or any active component hereof.

An interesting aspect of the invention pertains to a method for preventing and/or reducing overweight or obesity in a subject comprising administering a therapeutically effective amount, as described above, of a flaxseed product or any active component hereof as defined above.

In a further aspect, the present invention provides a hydrated and/or heat-treated flaxseed as a medicament. It follows from the above that the active ingredient increases faecal fat excretion from the gastrointestinal tract (has a fat retaining capacity). Hence, useful applications include use of a flaxseed product, as defined herein, for increasing faecal fat excretion, for medical treatment of overweight and obesity as well as for prevention and cosmetic treatment of overweight. And further more, there is provided a method for preparing a dietary supplement, food product, beverage product or combinations thereof comprising formulating hydrated and/or heat treated flaxseed as a food ingredient or a dietary supplement for increasing faecal fat excretion in a mammal.

A further aspect of the present invention relates to a pharmaceutical composition comprising the flaxseed product as previously defined. The composition may be formulated as a food ingredient, dietary supplement, a herbal compound or a pharmaceutical composition comprising any acceptable carrier, vehicle or diluent. Preferably, the composition is formulated for oral administration.

Suitably, especially for pharmaceutical use, a composition is stable for long term storage, such as at least 6 months at ambient conditions, e.g. at 25° C. and 60% RH, protected from day light. Longer storage periods may be desirable and in preferred embodiments the composition is stable for up to 2 years, including up to 1 year.

A still further aspect of the present invention relates to a method of preventing and/or reducing overweight or obesity in a subject, said method comprising administering a composition comprising a flaxseed product and/or the food and/or beverage product comprising a flaxseed product of the invention to said subject, as defined above.

Finally, there is provided a method of preventing or treating obesity comprising administering to a person suffering from obesity an effective amount of a composition comprising a flaxseed product as defined herein.

The following examples are included to demonstrate particular embodiments of the invention. However, those of skill in the art should, in view of the present disclosure, appreciate that many changes can be made in the specific embodiments which are disclosed and still obtain a like or similar result without departing from the spirit and scope of the invention. The following examples are offered by way of illustration and are not intended to limit the invention in any way. The invention will now be described in further details in the following non-limiting examples and FIGURE, wherein.

EXAMPLES

Example 1

Study of Whole Flaxseeds and the Effect on the Amount of Digested Fat from the Whole Diet in Healthy Young Men A common strategy for reducing the risk of overweight and obesity has been to reduce the average energy intake by lowering the fat intake. An additional strategy may be to consume foods with a low digestibility. It is well established that the dietary fiber content of the diet is an important determinant of the digestibility of energy and energy-contributing macronutrients.

The concept of partial digestibility was first introduced in animal energetics to describe differences in overall digestible nutrients when a supplement was added to a basal diet (Kleiber, 1987). Later, the concept was applied to human diets. The partial digestible energy values for unavailable carbohydrates (UC) in a number of human diets have been calculated. Values were found in the range from −20 to +10 kJ/g UC (Livesey, 1990). The negative values can be explained by the additional losses of especially protein and fat to feces associated with diets high in UC.

The aim of the present study was to measure the effects on the daily amounts of digested fat when whole sunflower seeds or flaxseeds were incorporated into bread and consumed as part of a whole diet by healthy subjects. A specific objective was to calculate the partial digestible energy value of whole sunflower seeds and flaxseeds, respectively.

1.1 Subjects and Methods 1.1.1 Subjects

Thirteen healthy male adults were recruited for the study from universities in Copenhagen. Their age (mean±SD) was 24.6±2.7 years and their BMI was 22.5±1.7 kg/m². None of the subjects used medicine regularly and all were non-smokers. The subjects were instructed to keep their physical activity levels constant and to abstain from alcohol throughout the study. The subjects were weighed at the beginning of each intervention period and at the end of the last intervention period. All subjects were given written and oral information about the study before signing an informed consent. The protocol was approved by the Municipal Ethical Committee of Copenhagen and Frederiksberg (Journal no. KF 01-070/01). Two subjects were excluded from the study due to missing values and use of antibiotics, respectively.

1.1.2 Study Design

The study comprised 4 intervention periods of 7 days each, separated from each other by a 7 day wash-out period where the subjects consumed their own diet. The subjects were assigned to one of 4 dietary interventions in a random crossover design. During the intervention periods, all subjects received the same basal weight maintenance diet comprising a rotating menu plus 300 g of rye bread composed as described below. The only dietary difference during the intervention periods was the consumption of the four different types of rye bread. During the study the participants lived at home but came to The Department of Human Nutrition to collect their food every day except for weekends.

1.1.3 Diets

The diets were composed of food items typical for a Danish diet, but meeting the Nordic Nutrient Recommendations for macronutrient intake: Protein E % 10-15; Fat E % below 30; carbohydrate E % 55-60 and dietary fiber intake 3 g/MJ. Three daily basal menus were composed (Table 1.1) and distributed in rotation to the subjects during the intervention periods to ensure that the only dietary difference between each intervention period was the rye bread.

TABLE 1.1

Composition of the 3 menus of the basal diet.

| Dietary composition, g | | | |
|---|---|---|---|
| White bread | 60 | 60 | 60 |
| Butter | 25 | 25 | 20 |
| Cheese, low-fat | 40 | 40 | 40 |
| Raspberry marmalade | 30 | 30 | 30 |
| Sliced ham | 35 | 35 | 35 |
| Liver pâté | 30 | — | 30 |
| Salami | — | 30 | — |
| Roast beef | 35 | — | 35 |
| Smoked turkey | — | 35 | — |
| Cucumber, raw | 50 | — | 50 |
| Tomato, raw | — | 70 | — |
| Apple, raw | 150 | — | 150 |
| Pear, raw | — | 150 | — |
| Orange juice | 500 | 500 | 500 |
| Milk, low-fat | 250 | 250 | 250 |
| Goulash | 385 | — | — |
| Carbonate | — | 190 | — |
| Bolognaise | — | — | 270 |
| Rice | 210 | — | — |
| Pasta | — | 200 | 245 |
| Chocolate | 55 | 45 | 60 |
| Candy | 70 | 70 | 50 |
| Chemical composition[1] | | | |
| Gross energy, MJ | 11.443 | 9.548 | 10.026 |
| Fat, g | 99.2 | 75.4 | 80.0 |
| Dietary fiber, g | 16.8 | 12.6 | 11.8 |

[1]The values for the chemical composition are gross values obtained by direct chemical analyses Four different rye breads were composed (Table 1.2):

C: Whole grain rye bread (Control),

SF: Control with sunflower seeds (SF),

FS: Control with flaxseeds (FS), and

SF/FS: Low extraction rate rye bread with SF and FS

The test rye breads C, SF and FS were made from whole grain milled rye flour and sourdough whereas the test rye bread SF/FS was made from low extraction rate rye flour (i.e. milled rye flour minus the rye bran) and sourdough. Sunflower seeds (6.2 g/100 g bread) and flaxseeds (6.2 g/100 g bread) substituted the whole grain milled rye flour in rye bread SF and FS, respectively whereas in rye bread SF/FS, sunflower seeds (6.8 g/100 g bread) and flaxseeds (6.1 g/100 g bread) substituted the low extraction rate rye flour. The rye breads were produced according to the traditionally procedure using sourdough. Sunflower seeds and flaxseeds were hydrated in water for 2 hours before dough making. After mixing all the ingredients slowly for 10 minutes the dough rested for another 10 minutes before it was divided into bread pans. The dough was subjected to rising for 72 minutes in a rising chamber at 30° C. and 85% relative humidity before it was baked for 72 minutes at 220° C.

TABLE 1.2

Composition of test rye breads (per 100 g bread)

| Ingredients | Rye bread C[1] | Rye bread SF[2] | Rye bread FS[3] | Rye bread SF/FS[4] |
|---|---|---|---|---|
| Whole grain milled rye flour | 40.8 | 31.6 | 32.5 | — |
| Rye flour, 67% extraction rate | — | — | — | 27.0 |
| Sourdough | 20.7 | 22.6 | 20.7 | 7.6 |
| Water | 19.6 | 19.0 | 19.3 | 30.0 |
| Rye flour, leaven | 17.3 | 18.8 | 19.3 | 6.4 |
| Squeezed whole grain rye | — | — | — | 11.1 |
| Sunflower seeds | — | 6.2 | — | 6.8 |
| Flaxseeds | — | — | 6.2 | 6.1 |
| Malt | — | — | — | 3.3 |
| Salt | 1.3 | 1.3 | 1.3 | 1.2 |
| Yeast | 0.2 | 0.5 | 0.5 | 0.6 |
| Vinegar | — | — | — | 0.7 |

TABLE 1.2-continued

Composition of test rye breads (per 100 g bread)

|  | Rye bread C[1] | Rye bread SF[2] | Rye bread FS[3] | Rye bread SF/FS[4] |
|---|---|---|---|---|
| Chemical composition[5] | | | | |
| Gross energy, kJ | 910 | 1074 | 1008 | 1138 |
| Fat, g | 1.8 | 5.1 | 4.0 | 7.3 |
| Dietary fiber, g | 8.1 | 8.1 | 8.6 | 6.5 |

[1]Rye bread C: whole grain rye bread (Control)
[2]Rye bread SF: control + sunflower seeds (SF)
[3]Rye bread FS: control + flaxseeds (FS)
[4]Rye bread SF/FS: low extraction rate rye bread + SF + FS
[5]The values for the chemical composition are gross values obtained by direct chemical analyses.

The breads were cooled for 1 hour before packing. The rye bread C and SF/FS were commercially available in Denmark whereas rye bread SF and FS were composed for the present study. Each subject received 300 g of rye bread per day besides the basal diet, which was given in amounts to ensure that the total daily energy needs as estimated by the method by WHO (1985) of each subject were met. The subjects were instructed to eat all the food items delivered and to return any food items not consumed.

1.1.4 Collection of Faecal Samples and Measurements of Transit Time

Transit time was estimated using the single stool method of Cummings & Wiggins (1976). At breakfast on day 4, 5, and 6, the subjects were given a dose (60 markers) of radio-opaque markers with a specific gravity between 1.25 and 1.60 (Medi-Fact, Göteborg), with a different shape of marker each day. The first stool passed after rising on day 7 of each intervention period was collected in plastic containers and immediately delivered to the Department of Human Nutrition. The faecal samples were weighed and frozen immediately after delivery. The content of markers was analysed by x-ray. The exact time for intake of the plastic markers and collection of stool together with the amount of the two markers present in the greatest amounts, were used to estimate the mean transit time for each subject.

1.1.5 Chemical Analysis

The 3 basal menus, the 4 test breads and all stool samples were freeze-dried and homogenised before further chemical analyses, all carried out in duplicates. Dry matter content was determined after drying for 20 h at 85° C. for the 3 basal menus and the test breads and for 20 h at 100° C. for the faecal samples. Gross energy was determined by adiabatic bomb calorimetry calibrated with benzoid acid (IKA C 400 A). Fat was determined gravimetrically after acid hydrolysis to liberate saponified fatty acids according to the method of Bligh & Dyer (1959). Dietary fibre was defined as non-starch polysaccharides (NSP) and the content in the basal menus and the test breads was determined as alditol acetates by gas-liquid chromatography (Knudsen, 1997).

1.1.6 Calculations and Statistical Analysis

The average daily stool weight of each subject was estimated from the weight of the morning stool on day 7 corrected to a theoretical marker output of 60 markers/d. Absorption of fat and energy was calculated as the difference between nutrient intake and faecal loss, expressed as a percentage of nutrient intake.

Partial-digestibility-energy values ($DE_{partial}$) of sunflower seeds and flaxseeds were calculated according to the formula for substances replacing another substance with an apparent digestibility less than 1.0 (Livesey, 1990):

$$DE_{partial}(kJ/g) = \Delta H_{seed}(1-Z),$$

where $\Delta H_{seed}$ is the heat of combustion (=gross energy) of sunflower seeds and flaxseeds, respectively and $$Z = \Delta FE/\Delta GE + (1 - D_o),$$

where $\Delta FE$ and $\Delta GE$ are the changes in faecal energy and changes in gross energy intakes between the basal diet+bread C and the basal diet+bread SF/FS, respectively. $D_o$ is the apparent digestibility of energy of the substance being replaced, in this case rye flour with a $D_o$ of 0.92 (Livesey, 1990).

All statistical analyses were performed in SAS® System for Windows (release 8.2, SAS institute inc., Cary, N.C.). Analysis of variance was performed in the procedure MIXED with faecal dry weight, faecal water content, transit time, intake, faecal excretion, digestibility and digested amount of fat and energy, respectively evaluated as dependent variables. Type of bread, period and interaction between the two were evaluated as independent fixed variables. Subjects were included as an independent random variable. Where significant differences were found, paired t-test for comparison of the four diets was applied using Tukey's post hoc test. The results in tables are given as the least square mean±standard error of the estimate (SEE).

1.2 Results

The inclusion of the sunflower seeds and flaxseeds were reflected in the measured fat and energy content of the test breads. Fat content per 100 g bread ranged from 1.8 g in rye bread C to 7.3 g in rye bread SF/FS and energy content per 100 g bread ranged from 910 kJ in rye bread C to 1138 kJ in rye bread SF/FS (Table 1.2).

Faecal dry weight and faecal water content were significantly affected by diet (Table 1.3). The faecal dry weight (mean±SEE) was significantly higher in subjects receiving the basal diet+rye bread FS (84.0±6.6 g) and the basal diet+rye bread SF/FS (72.5±6.6 g) compared to the basal diet+rye bread C (62.0±6.6 g) and the basal diet+rye bread SF (61.1±6.6 g). The average transit time (mean±SEE) of 33.3±2.0 hours was not affected by diet.

Gross fat intake was significantly affected by diet with the highest average fat intake of (mean±SEE) 121±2.4 g/day in the subjects consuming the basal diet+rye bread SF/FS and the lowest fat intake of 104±2.4 g/day in the subjects consuming the basal diet+rye bread C (Table 1.4). Faecal fat excretion was significantly affected by diet, ranging from a daily excretion of (mean±SEE) 8.6±1.6 g in subjects consuming the basal diet+rye bread C to 25.0±1.5 g in subjects consuming the basal diet+rye bread SF/FS. Fat digestibility was significantly affected by diet with the lowest value of 76.0±2.0% in the basal diet+rye bread SF/FS and the highest value of 92.1±1.9% in the subjects consuming the basal diet+rye bread C. The amount of digested fat was significantly affected by diet with the lowest amount of absorbed fat (mean±SEE) in the subjects consuming the basal diet+rye bread FS (88.8±2.8 g/d).

TABLE 1.3

Faecal dry weight and faecal water content and transit time in healthy subjects consuming a basal diet and C bread: whole grain rye bread (Control), SF bread: control + sunflower seeds (SF), FS bread: control + flaxseeds (FS), and SF/FS bread: low extraction rate rye bread + SF + FS (mean ± SEE) (n = 11)

| | Basal diet + C bread | Basal diet + SF bread | Basal diet + FS bread | Basal diet + SF/FS bread | p[1] |
|---|---|---|---|---|---|
| Faecal dry weight, g/d | 62.0 ± 6.6$^{bc}$ | 61.1 ± 6.6$^{bc}$ | 84.0 ± 6.6$^{a}$ | 72.5 ± 6.6$^{ac}$ | 0.026 |
| Faecal water content, % | 77.8 ± 1.01$^{a}$ | 74.8 ± 1.01$^{b}$ | 74.3 ± 1.01$^{b}$ | 70.1 ± 0.94$^{c}$ | <0.001 |
| Transit time, hours | 35.2 ± 2.0 | 31.6 ± 2.0 | 33.3 ± 2.0 | 34.8 ± 2.0 | NS |

Significant differences between values within a row are indicated with different superscript letters Gross energy intake mirrored the gross fat intake (Table 1.5). Gross energy intake was significantly affected by diet with a significantly higher gross energy intake (mean±SEE) of 15.3±0.29 MJ/d in subjects consuming the basal diet+rye bread SF/FS compared to the other diets. Faecal energy excretion was significantly affected by diet with the highest faecal energy excretion in the subjects consuming the basal diet+rye bread SF/FS and in the subjects consuming the basal diet+rye bread FS. Energy digestibility was significantly affected by diet with the highest values (mean±SEE) in the subjects consuming the basal diet+rye bread C (91.7±1.0%) and the basal diet+rye bread SF (90.8±1.0) compared to the subjects consuming the basal diet and rye bread FS (87.3±1.0%) and the basal diet and rye bread SF/FS (88.6±1.0%), respectively. The amount of digested energy was significantly different between the dietary groups, with the lowest value in the subjects consuming the basal diet+FS bread.

TABLE 1.4

Gross fat intake, faecal fat excretion, fat digestibility and amount of digested fat in healthy subjects consuming a basal diet and C bread: whole grain rye bread (Control), SF bread: control + sunflower seeds (SF), FS bread: control + flaxseeds (FS), and SF/FS bread: low extraction rate rye bread + SF + FS (mean ± SEE) (n = 11)

| | Basal diet + C bread | Basal diet + SF bread | Basal diet + FS bread | Basal diet + SF/FS bread | p[1] |
|---|---|---|---|---|---|
| Gross fat intake, g/d | 104 ± 2.4$^{d}$ | 114 ± 2.4$^{b}$ | 111 ± 2.4$^{c}$ | 121 ± 2.4$^{a}$ | <0.001 |
| Faecal fat excretion, g/d | 8.6 ± 1.6$^{c}$ | 15.4 ± 1.5$^{b}$ | 22.2 ± 1.5$^{a}$ | 25.0 ± 1.5$^{a}$ | <0.001 |
| Fat digestibility, % | 92.1 ± 1.9$^{a}$ | 85.9 ± 2.0$^{b}$ | 80.7 ± 2.0$^{b}$ | 76.0 ± 2.0$^{b}$ | <0.001 |
| Digested fat, g/d | 95.4 ± 2.8$^{a}$ | 98.8 ± 2.8$^{a}$ | 88.8 ± 2.8$^{b}$ | 95.6 ± 2.8$^{a}$ | <0.001 |

[1]Significant differences between values within a row are indicated with different superscript letters

TABLE 1.5

Gross energy intake, faecal energy excretion, energy digestibility and digested energy in healthy subjects consuming a basal diet and C bread: whole grain rye bread (Control), SF bread: control + sunflower seeds (SF), FS bread: control + flaxseeds (FS), and SF/FS bread: low extraction rate rye bread + SF + FS (mean ± SEE) (n = 11)

| | Basal diet + C bread | Basal diet + SF bread | Basal diet + FS bread | Basal diet + SF/FS bread | p[1] |
|---|---|---|---|---|---|
| Gross energy intake, MJ/d | 14.7 ± 0.29$^{d}$ | 15.1 ± 0.29$^{b}$ | 15.0 ± 0.29$^{c}$ | 15.3 ± 0.29$^{a}$ | <0.001 |
| Faecal energy excretion, MJ/d | 1.22 ± 0.14$^{c}$ | 1.39 ± 0.14$^{bc}$ | 1.87 ± 0.14$^{a}$ | 1.74 ± 0.14$^{ab}$ | 0.002 |
| Energy digestibility, % | 91.7 ± 1.0$^{a}$ | 90.8 ± 1.0$^{a}$ | 87.3 ± 1.0$^{b}$ | 88.6 ± 1.0$^{ab}$ | 0.003 |
| Digested energy, MJ/d | 13.4 ± 0.32$^{ab}$ | 13.8 ± 0.32$^{a}$ | 13.1 ± 0.32$^{b}$ | 13.6 ± 0.32$^{a}$ | 0.004 |

[1]Significant differences between values within a row are indicated with different superscript letters Gross energy of the sunflower and flaxseeds was 29.4 and 24.7 kJ/g, respectively. The partial digestible energy values of the sunflower seeds and the flaxseeds were 19.8 and −27.3 kJ/g, respectively (Table 1.6).

TABLE 1.6

Partial digestible energy values of sunflower and flaxseeds

|  | Sunflower seeds | Flaxseeds |
| --- | --- | --- |
| Gross energy (kJ/g) | 29.4 | 24.7 |
| Partial digestibility (%) | 0.67 | −1.10 |
| Partial digestible energy value (kJ/g) | 19.8 | −27.3 |

1.3 Discussion

The results from the present study suggest that flaxseeds substituting 6% of the whole grain rye flour in rye bread has a fat binding capacity within the gastrointestinal tract. This results in an increase in the faecal fat excretion exceeding the fat intake from the flaxseeds themselves and in a negative partial digestible energy value for flaxseeds of −27.3 kJ/g. As "partial digestible energy" expresses how much energy is digested from the whole diet when one gram of seeds are added, the result convincingly illustrates that the addition of flaxseeds to the diet resulted in a reduction of digestible energy whereas sunflower seeds did not display the same properties. Thus, the results are important findings in relation to fat intake, fat digestion and energy balance and thus in body weight regulation/management.

Sunflower seeds and flaxseeds are characterised by their high content of dietary fibre (DF) and dietary fat and low content of water, all factors contributing to the high energy density of the seeds. From a health perspective, the use of sunflower seeds and flaxseeds in commercial bread production systems has been augmented by their relative high content of dietary fibre. However, the high fat content of both sunflower seeds and flaxseeds has been claimed to counterbalance the nutritional value of the seeds.

It has repeatedly been demonstrated that dietary fibre is effective in reducing mouth to anus transit time and in increasing stool bulk. In the present study the total average intake of DF between the dietary groups varied between 35.5 and 42.0 g DF/d (results not shown) but no significant differences were found between the dietary groups with respect to the mean transit time (Table 1.3). The method used for measuring mean transit time in the present study is based on the principle that a dose of markers with a similar gravity as cellulose fibre given continuously with meals is recovered in the stool. Using the continuous marker method over several weeks it has been shown that a dose of 20 or 80 markers daily resulted in similar estimates of transit time and that the results correlated significantly with the single stool methods applied in the present study. In a separate study using 60 markers/d, as applied in this study, the recovery rate was found to be as high as 95%±9 (Sandstrom et al. 2000). The transit time in the present study was 33.3±2.3 h (mean±SD), which is comparable to the transit time found in earlier investigations on healthy young males consuming a diet rich in DF.

The flaxseed dietary fibre (called the mucilage) is a group of heterogenic polysaccharides present on the outside of the seed coat comprising mainly arabinoxylans (pentosans) and galacturonic acid. The present study confirms earlier observations that pentosans present as arabinoxylans in rye and ryebread have a particular stool bulking effect. The results further suggest that the arabinoxylans in the flaxseeds have an additive effect on faecal bulking, as seen by the significantly higher faecal dry matter in the subjects receiving the basal diets and the rye bread with the flaxseeds alone or in combination with sunflower seeds (Table 1.3). This concurs with the laxative effects of whole flaxseeds known and practiced since ancient times.

Upon hydration, the mucilage of flaxseeds expands extremely rapidly to many times its original dimensions and due to the suberized inner walls of the mucilaginous cells, the mucilage will migrate into the surrounding solution leading to a dramatic increase in the viscosity of the media. Studies on the effects on the blood-glucose-lowering effect of the flaxseed bread have suggested that flaxseed mucilage behaves like a typical viscous fibre in its ability to reduce postprandial blood glucose response (Wolever & Jenkins, 2001). Soluble fibre has been shown to be able to reduce the glycaemic responses by increasing the viscosity of the small intestinal contents and delaying the digestion and absorption of carbohydrates. The results of the present study suggest that the mucilage of flaxseeds may also interfere with the digestion and absorption of dietary fat possibly through a binding between the mucilage of the flaxseeds to the fat in the gastrointestinal tract, thereby reducing the overall digestibility of fat (table 1.4).

Considerable nutritional interest has been paid to the fat content of flaxseeds due to the high concentration of alpha-linoleic acid (ALA). Thus, ALA has been shown to exert positive effects on the serum lipid profile, fatty acid composition and platelet function in humans. But to our knowledge, no human studies have been conducted to examine the digestibility of the fat from whole flaxseeds.

A human trial testing the bioavailability of the 18:3n−3 from flaxseed has been described. Evaluation after a 4 week intervention period illustrated that the bioavailability of the 18:3n−3 seems as high from the flaxseed as from flaxseed oil (Cunnane et al. 1993).

Based on the results from the present study enrichment of food and beverages with whole or processed flaxseeds may be a useful strategy to reduce fat absorption in humans without compromising the palatability of the foods/beverages. These results have important implications for the digestible energy values used in food tables.

1.4 Conclusion

The present study demonstrated that flaxseed reduces fat absorption when consumed in amounts of 18 g/day by young healthy males. The fat binding capacity of flaxseeds results in a negative partial digestible energy value of −27 kJ/g.

Example 2

In Vitro Study of Flaxseed's Fat Binding and Fat Adsorbing Qualities

Example 1 showed the results of a human dietary intervention study conducted as a randomised, cross-over study with young, healthy subjects. The results of that study showed that faecal fat excretion after intake of a diet with rye bread containing flaxseed was significantly higher than fat excretion on a diet with rye bread without flaxseed, and this was not exclusively due to the difference in the fat content of rye bread. The study indicated that flaxseed contain components with effects on fat binding and fat absorption.

The aim of this study was clarification of the reasons for the fat binding and adsorbing effect in vitro of flaxseed, flaxseed as an ingredient in rye bread and flaxseed as an ingredient in rye bread as a part of a daily diet.

2.1 Material and Methods

2.1.1 Composition of the Test Material

The experimental test material:
1. Flaxseed
2. Rye bread with flaxseed
3. Rye bread without flaxseed
4. Rye flour
5. Diet with rye bread without flaxseed
6. Diet with rye bread with flaxseed The test rye breads were made from whole grain milled rye flour and sourdough. Flaxseeds (6.2 g/100 g bread) substituted the whole grain milled rye flour in rye bread. The rye breads were produced according to the traditionally procedure using sourdough. Whole flaxseeds were hydrated in water for 2 hours before dough making. After mixing all the ingredients slowly for 10 minutes the dough rested for another 10 minutes before it was divided into bread pans. The dough was subjected to rising for 72 minutes in a rising chamber at 30° C. and 85% relative humidity before it was baked for 72 minutes at 220° C. The breads were cooled for 1 hour before packing.

The composition of a full diet with flaxseed and a full diet without flaxseed were as described in Example 1.

2.1.2 Methods for Analysing the Test Material

1. Pre-milling of freeze-dried test material
2. Fat extraction of test material by supercritical fluid extraction (SFE) with and without modifier to provide data on the total content of triglycerides and lipids.
3. In vitro digestion using pepsin/pancreatin enzymes (Enzyme Digestible Organic Matter (EDOM) method for the isolation of indigestible material.
4. Fat extraction of the indigestible material by supercritical fluid extraction (SFE) with and without modifier.

2.1.3 Materials

The enzymes used for the EDOM method comprised pepsin (from porcine gastric mucosa, 2000 FIP U/g, Merck 7190), pancreatin (from porcine pancreas, grade VII, activity 4×USP, P-1750, Sigma). All other chemicals were of pro analysis grade and purchased from Sigma-Aldrich (St. Louis, Mo.).

2.1.4 Sample Preparation

Flaxseed, rye flour, rye-bread with flaxseed, ordinary rye-bread, the two full diets was freeze-dried, grounded with a coffee grinder and sieved resulting in particles of 0.7 mm or less sold.

2.1.5 In Vitro Digestion

The in vitro digestion was performed according to EDOM descriptions with few adjustments. In short, ground and sieved samples (0.5 g) was carefully suspended in phosphate buffer A (25 mL; 0.1 M; pH 6) followed by addition of HCl (10 mL; 0.2 M) and pepsin suspension (1 mL; 25 mg/mL in 0.2 M HCl). The pH of the suspension was adjusted to 2 with HCl (1 M) or NaOH (1 M). The suspension was added sodium azid (0.5 mL; 0.05%) and incubated for 75 minutes in 40° C. water bath with automatic shaking. The pepsin digest was then added NaOH (5 mL; 0.6 M) and phosphate buffer B (10 mL; 0.2 M; pH 6.8). Then pH was adjusted to pH 6.8 with NaOH (1 M) or HCl (1 M). A suspension of pancreatic enzymes (1 mL; 100 mg/mL in phosphate buffer B) was added and the digestion was continued for 18 hour in 40° C. water bath with automatic shaking. After incubation the digested sample was centrifuged (6000 rpm in 10 min, 4° C.) and the precipitate and supernatant were separated and freeze dried.

In vitro digestion by the EDOM method gives a measure of undigested test material. The undigested test material is generally denoted dietary fibre, where the greater part originates from the undigested polysaccharides, lignin and other types of associated indigestible plant materials.

Fat extraction gives information on the oil/lipid content of the test material. The extraction is performed both with and without modifier. The very lipophile fat fraction is obtained without modifier, whilst extraction with modifier gives the fraction with more amphiphilic compounds such as phospholipids.

The second fat extraction using indigestible material obtained from the EDOM method give a measure of the amount of fat adsorbed in the indigestible part of the test material.

2.1.6 SFE with $CO_2$ (SFE-$CO_2$)

A laboratory-scale supercritical fluid extraction system was used for the oil and lipid extractions. Carbon dioxide (99.9% purity) was compressed to supercritical fluid by adjusting pressure and temperature to obtain the desired properties for oil and lipid extraction. Ground and sieved sample (2 g) was loaded into the extraction vessel and placed in the extraction cell. The extracts were collected in glass tubes. The extraction was performed with $CO_2$ at 600 bar with a flow rate of 4 L/min. The temperature in the oven was held at 60° C. and the valve temperature was 90° C. The oil extraction was performed for 30 minutes.

2.1.7 SFE with EtOH as Modifier

Following the SFE-$CO_2$ extraction, the extraction was continued with addition of EtOH as modifier to the supercritical fluid. The extraction condition was as previous described for the SFE-$CO_2$. The flow rate of EtOH was 1 mL/min resulting in an EtOH of approximately 10%. The SFE-modifier fraction was collected in a separate glass tube. This lipid extraction was performed for 30 minutes.

2.2. Results

The SFE analysis of the test materials show that the oil content in flaxseed is high, as expected and in addition, the oil content of the rye bread with flaxseed is higher than that of the rye bread without flaxseed (Table 2.1). Analysis of the first fat extraction (SFE analyses) showed that the fat content in the test materials was dominated by triglycerides (Table 2.1).

TABLE 2.1

Dry matter content (g/100 g) and fat (oil and other lipids) extracted by SFE of the test material shown as % of total extracted oil and lipid of initial amount of dry matter (Mean ± SD; n = 2).

| | Flaxseed (%) | Rye bread with flaxseed (%) | Rye bread without flaxseed (%) | Rye flour (%) | Diet with rye bread without flaxseed* (%) | Diet with rye bread with flaxseed (%) |
|---|---|---|---|---|---|---|
| Dry matter content[1] | 93 | 56 | 59 | 89 | 31 | 32 |

TABLE 2.1-continued

Dry matter content (g/100 g) and fat (oil and other lipids) extracted by SFE of the test material shown as % of total extracted oil and lipid of initial amount of dry matter (Mean ± SD; n = 2).

|  | Flaxseed (%) | Rye bread with flaxseed (%) | Rye bread without flaxseed (%) | Rye flour (%) | Diet with rye bread without flaxseed* (%) | Diet with rye bread with flaxseed (%) |
|---|---|---|---|---|---|---|
| SFE CO$_2$ | 31.4 ± 4.0 | 2.7 ± 0.4 | 0.2 ± 0.1 | 0.8 ± 0.1 | 10.4 ± 0.5 | 10.9 ± 0.5 |
| SFE CO$_2$ + EtOH | 2.9 ± 0.8 | 0.8 ± 0.0 | 0.5 ± 0.1 | 0.6 ± 0.1 | 2.7 ± 0.5 | 2.6 ± 0.2 |
| Total | 34.3 ± 3.2 | 3.5 ± 0.5 | 0.7 ± 0.1 | 1.3 ± 0.0 | 13.1 ± 0.7 | 13.4 ± 0.6 |

*Mean ± SD;
n = 3;
[1] Single determination.

Figure 1:
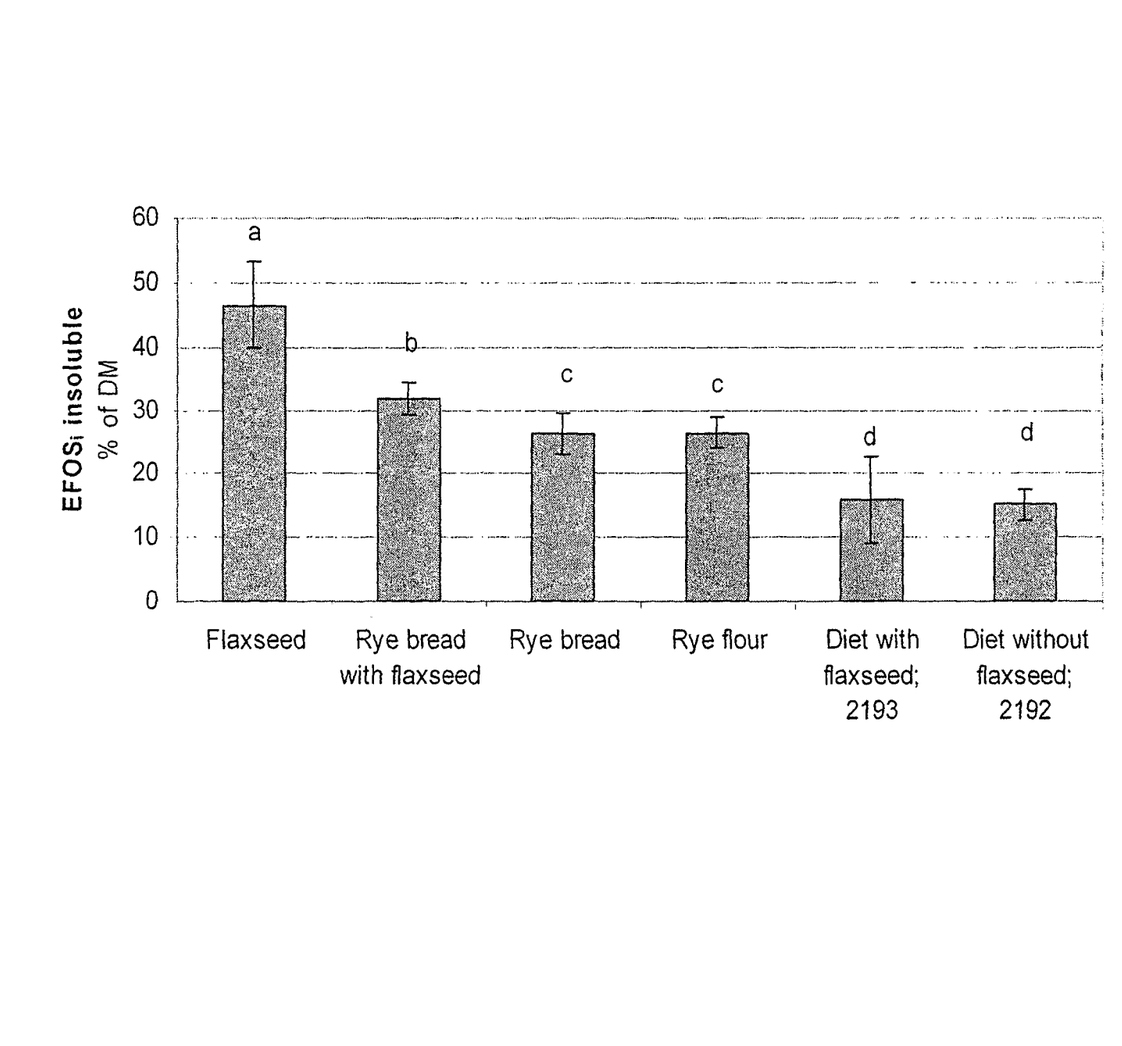
FIG. 1 shows the insoluble undigested material after in vitro digestion ($EDOM_i$) of flaxseed, rye bread with flaxseed, rye bread without flaxseed, rye flour, diet without flaxseed (diet 2192) and diet with flaxseed (diet 2193) expressed as % of dry matter (Mean±SD; n=3). a, b, c, d: Different letters indicate significant differences (P<0.05; t-test).

The amount of undissolved material after in vitro digestion (EDOM$_i$) of flaxseed, rye bread with flaxseed, rye bread without flaxseed, rye flour, diet without flaxseed and diet with flaxseed showed significant differences as shown in FIG. 1.

The flaxseed sample resulted quantitatively in the largest amount of insoluble material after in vitro EDOM digestion. However, of special interest is the share of insoluble material obtained by EDOM of rye bread with and without flaxseed. The results show significant higher amount of insoluble material obtained after EDOM of rye bread with flaxseed compared to that obtained from rye bread without flaxseed (P=0.038; t-test; FIG. 1). No significant differences in amount of insoluble EDOM$_i$ material were found between the full diets with and without flaxseed.

The total content of oil and lipids in the soluble and insoluble parts after in vitro digestion are shown in Table 2.2. The predominating part of the oil and lipid from flaxseed are found in the insoluble material of EDOM$_i$ (70%) where it most likely is adsorbed to other non-digestible material. In general, a higher content of oil and lipids is seen in the insoluble part of the EDOM$_i$ material in the products containing flaxseed, whilst the oil and lipid content in the soluble EDOM$_i$ fractions are similar with and without flaxseed. The amount of oil and lipid in the insoluble EDOM$_i$ fraction were significant higher from rye bread with flaxseed than obtained from rye bread without flaxseed (P=0.032; t-test; Table 2.2).

The results of Table 2.2 also shows a significant higher amount of oil and lipid in the insoluble EDOM$_i$ fraction of the diet containing flaxseed compared to that obtained with the diet without flaxseed (P=0.013; t-test).

In addition, comparing the results of Table 2.1 and 2.2, it can be seen that approximately 65% of the total lipid and oil in the test material are recovered after EDOM$_i$. This suggests that approximately ⅓ of the initial amount of oil and lipid from flaxseed is oxidised or broken down during the in vitro digestion process. This result indicates that the main part of the fat contained in flaxseed is not digestible in the gastrointestinal tract of a mammal.

Table 2.3 show the actual composition and thus the content of oil and lipid of the insoluble EDOM. The results reveals that approximately one third of the insoluble EDOM$_i$ material of flaxseed consists of lipid and oil, whereas only approximately 5% of the insoluble EDOM$_i$ material of rye bread is oil and lipid constituents.

The significant difference between rye bread with or without flaxseed, and between the diets with rye bread with or without flaxseed, disappears when the oil and lipid content is expressed as % of the insoluble indigestible material (Table 2.3), though the tendency remains. The most likely explanation for this is the small number of repetitions.

TABLE 2.2

Total oil and lipid obtained by SFE of the soluble and insoluble parts of the indigestible dry matter in flaxseed, rye bread with flaxseed, rye bread without flaxseed, rye flour, diet with flaxseed and diet without flaxseed shown as % of dry matter (Mean ± SD; n = 3).

|  | Flaxseed (%) | Rye bread with flaxseed (%) | Rye bread without flaxseed (%) | Rye flour (%) | Diet with rye bread without flaxseed (%) | Diet w. rye bread with flaxseed (%) |
|---|---|---|---|---|---|---|
| EDOM$_i$ soluble | 6.56 ± 2.16[a] | 1.86 ± 0.50[b] | 1.43 ± 0.35[b] | 0.17 ± 0.03[c] | 5.75 ± 1.06[a] | 5.01 ± 1.27[a] |
| EDOM$_i$ insolub. | 15.75 ± 3.26[a] | 2.26 ± 0.33[b] | 1.07 ± 0.64[c] | 1.51 ± 0.79[b,c] | 3.17 ± 0.42[d] | 4.20 ± 0.29[e] |
| Total | 22.31 ± 4.49[a] | 4.12 ± 0.17[b] | 2.50 ± 0.98[c] | 1.67 ± 0.81[c] | 8.91 ± 1.43[d] | 9.27 ± 1.44[d] |

[abcde]Different letters horizontally in the table indicate significantly different values (P < 0.05; t-test)

TABLE 2.3

Total oil and lipid in the insoluble part of the indigestible material in flaxseed, rye bread with flaxseed, rye bread without flaxseed, rye flour, diet with flaxseed and diet without flaxseed shown as % of the insoluble dry matter after in vitro digestion (Mean ± SD; n = 3).

|  | Flaxseed (%) | Rye bread with flaxseed (%) | Rye bread without flaxseed (%) | Rye flour (%) | Diet with rye bread without flaxseed (%) | Diet with rye bread w. flaxseed (%) |
|---|---|---|---|---|---|---|
| EDOM$_i$ insolubl. | 32.69 ± 2.16$^a$ | 7.17 ± 0.72$^b$ | 4.13 ± 2.34$^b$ | 5.69 ± 2.92$^b$ | 20.62 ± 2.48$^c$ | 29.44 ± 8.89$^{a,c}$ |

$^{abc}$Different letters indicate significantly different values (P < 0.05; t-test)

2.4. Conclusion

The results in Table 2.2 show that the fat binding and/or the fat adsorption (expressed as % of dry matter) were significantly higher in rye bread with flaxseed (4.12±0.17) than in rye bread without flaxseed (2.50±0.98). Significant higher amount of oil and lipid were, in addition, found in the insoluble indigestible fraction of the diet with rye bread with flaxseed (4.20±0.29) compared to that obtained with the diet with rye bread without flaxseed (3.17±0.42). This is primarily due to the higher fat content in the insoluble part of the indigestible material. Compositional, there is a tendency of higher ratio of oil and lipid in insoluble indigestible products containing flaxseed compared with those not containing flaxseed (Table 2.3). The higher amount of oil and lipid in the insoluble EDOM$_i$ fraction from products containing flaxseed is in agreement with findings of higher lipid content in faecal samples from subjects giving flaxseed-containing diets. The results thus support the findings of the human intervention study (Example 1) where flaxseed resulted in fat binding/fat adsorbing effect.

REFERENCES

Bligh E G & Dyer W J. 1959. A Rapid Method of Total Lipid Extraction and Purification. Canadian Journal of Biochemistry and Physiology. 37:911-7.
Cummings J H & Wiggins H S. 1976. Transit through the gut measured by analysis of a single stool. Gut. 17:219-23.
Cunnane S C, Ganguli S, Menard C et al. 1993. High alpha-linolenic acid flaxseed (Linum usitatissimum): some nutritional properties in humans. Br J. Nutr. 69:443-53.
FAO/WHO. FAO/WHO/UNU. 1985. Energy and protein requirements. Technical Report Series 724. WHO Geneva.
Kleiber M. The Fire of Life. 1987. An Introduction to Animal Energetics.
Knudsen K E. 1997. Carbohydrate and lignin contents of plant materials used in animal feeding. Animal Feed Science Technology 67:319-38.
Livesey G. 1990. Energy values of unavailable carbohydrate and diets: an inquiry and analysis. Am J Clin Nutr 50:617-37.
Sandstrom B, Bugel S, McGaw B A, Price J & Reid M D. 2000. A high oat-bran intake does not impair zinc absorption in humans when added to a low-fiber animal protein-based diet. J Nutr 130:594-9.
Wolever T M S & Jenkins D J A. 2001. Effect of Dietary Fiber and Foods on Carbohydrate Metabolism. In: Spiller G A, ed. Dietary Fiber in Human Nutrition. CRC Press 321:60.

What is claimed is:

1. A method of decreasing the absorption of dietary fat in a mammal in need thereof, said method comprising: administering to said mammal a beverage product comprising a fraction of flaxseeds enriched in mucilage, wherein a total content of the fraction of flaxseeds enriched in mucilage is 1 to 50% by weight of said beverage product; whereby absorption of dietary fat by said mammal is decreased.

2. The method according to claim 1, wherein the mammal is a human.

3. The method according to claim 1, wherein the fraction of flaxseeds enriched in mucilage is treated by a process selected from the group consisting of hydration, heat-treatment, milling, grinding, and separation and combinations thereof.

4. The method according to claim 1, wherein said fraction of flaxseeds enriched in mucilage further comprises seed coats, arabinoxylans, or galacturonic acid or combinations thereof.

5. The method according to claim 1, wherein the fraction of flaxseeds enriched in mucilage is from one or more flaxseed varieties of the genus 'Linum' selected from the group consisting of Golden, Dufferin, Rahab, Verne, Clark, Culbert, culbert79, Flor, Linott, Linton, McGregor, Norlin, and NorMAn and combinations thereof.

6. The method according to claim 1, wherein the fraction of flaxseeds enriched in mucilage has a negative partial digestible energy value ranging from −1 to −40 kJ/g of the fraction of flaxseed.

7. The method according to claim 1, wherein said beverage product further comprises ground grains or whole grains of one or more of the species selected from the group consisting of sunflower, rye, wheat, maize, and soy and combinations thereof.

8. The method according to claim 1, wherein an amount of mucilage equivalent to the amount of mucilage present in 1-100 g of whole flaxseed is administered to said mammal daily.

9. The method according to claim 1, wherein the beverage product is administered to said mammal as part of a low fat diet.

10. The method according to claim 1, wherein said beverage product has been subjected to a heat treatment.

11. The method according to claim 1, wherein said beverage product is selected from the group consisting of a milk product, a vegetable product, and a semi-manufactured product and combinations thereof.

12. The method according to claim 1, wherein said beverage product has a concentration of fat that is at least 7% by weight.

13. The method of claim 1, wherein said fat originates from another food or beverage ingested prior to, concomitantly with or immediately after said beverage product.

14. The method of claim 1, wherein said fraction of flaxseeds enriched in mucilage is a water soluble fraction of hydrated flaxseeds.

15. The method of claim 1, wherein said fraction of flaxseeds enriched in mucilage consists essentially of mucilage.

16. The method according to claim 1, wherein said mammal is a human subject having a body mass index (BMI) of at least 25.

17. The method according to claim 1, wherein absorption of triglycerides in the mammal is decreased.

18. The method according to claim 1, wherein said mammal is a human subject having a body mass index (BMI) of at least 30.0.

19. The method according to claim 1, wherein the total content of the fraction of flaxseeds enriched in mucilage is 5 to 40% by weight of said beverage product.

20. The method according to claim 1, wherein the total content of the fraction of flaxseeds enriched in mucilage is 10 to 30% by weight of said beverage product.

21. The method according to claim 1, wherein the total content of the fraction of flaxseeds enriched in mucilage is 15 to 25% by weight of said beverage product.

22. A method of inhibiting weight gain of a mammal in need thereof, comprising:
    administering to said mammal a beverage product comprising a fraction of flaxseeds enriched in mucilage, wherein a total content of the fraction of flaxseeds enriched in mucilage is 1 to 50% by weight of said beverage product, thereby decreasing absorption of dietary fat in the gastrointestinal tract; and
    measuring the body weight of said mammal, whereby weight gain of said mammal is inhibited.

23. The method of claim 22, wherein said mammal is human.

24. The method of claim 22, wherein said fraction of flaxseeds enriched in mucilage consists essentially of mucilage.

25. The method of claim 22, wherein said fraction of flaxseeds enriched in mucilage is a water soluble fraction of hydrated flaxseeds.

26. The method according to claim 22, wherein said beverage product further comprises ground grains or whole grains of one or more of the species selected from the group consisting of sunflower, rye, wheat, maize, and soy and combinations thereof.

27. The method according to claim 22, wherein an amount of mucilage equivalent to the amount of mucilage present in 1-100 g of whole flaxseed is administered to said mammal daily.

28. The method according to claim 22, wherein the beverage product is administered to said mammal as part of a low fat diet.

29. The method according to claim 22, wherein said beverage product is selected from the group consisting of a milk product, a vegetable product, and a semi-manufactured product and combinations thereof.

30. The method according to claim 22, wherein said beverage product has a concentration of fat that is at least 7% by weight.

31. The method according to claim 22, wherein said mammal is a human subject having a body mass index (BMI) of at least 25.

32. The method according to claim 22, wherein absorption of triglycerides in the mammal is decreased.

33. The method according to claim 22, wherein said mammal is a human subject having a body mass index (BMI) of at least 30.0.

34. The method according to claim 22, wherein the total content of the fraction of flaxseeds enriched in mucilage is 5 to 40% by weight of said beverage product.

35. The method according to claim 22, wherein the total content of the fraction of flaxseeds enriched in mucilage is 10 to 30% by weight of said beverage product.

36. The method according to claim 22, wherein the total content of the fraction of flaxseeds enriched in mucilage is 15 to 25% by weight of said beverage product.

* * * * *